United States Patent
Sakamoto (10) Patent No.: US 12,007,614 B2
(45) Date of Patent: Jun. 11, 2024

(54) MEDICAL OBSERVATION SYSTEM AND TRANSMISSION CABLE

(71) Applicant: Sony Olympus Medical Solutions Inc., Tokyo (JP)

(72) Inventor: Kenji Sakamoto, Tokyo (JP)

(73) Assignee: Sony Olympus Medical Solutions Inc., Tokyo (JP)

(*) Notice: Subject to any disclaimer, the term of this patent is extended or adjusted under 35 U.S.C. 154(b) by 0 days.

(21) Appl. No.: 17/799,934

(22) PCT Filed: Jan. 22, 2021

(86) PCT No.: PCT/JP2021/002295
§ 371 (c)(1),
(2) Date: Aug. 16, 2022

(87) PCT Pub. No.: WO2021/181914
PCT Pub. Date: Sep. 16, 2021

(65) Prior Publication Data
US 2023/0064925 A1    Mar. 2, 2023

(30) Foreign Application Priority Data
Mar. 11, 2020  (JP) ................................ 2020-042475

(51) Int. Cl.
*G02B 6/44* (2006.01)
*A61B 1/00* (2006.01)

(52) U.S. Cl.
CPC .............. *G02B 6/4401* (2013.01); *A61B 1/00* (2013.01)

(58) Field of Classification Search
CPC .. G02B 6/4401; G02B 6/4477; G02B 6/4416; A61B 1/00

USPC ......................................................... 385/100
See application file for complete search history.

(56) References Cited

U.S. PATENT DOCUMENTS

| | | | | |
|---|---|---|---|---|
| 2007/0280610 A1* | 12/2007 | Mallya | ................. | G02B 6/4416 385/101 |
| 2012/0241040 A1* | 9/2012 | Fogg | ...................... | H01B 7/046 138/172 |
| 2012/0281953 A1* | 11/2012 | Choi | .................... | G02B 6/4416 385/101 |
| 2013/0058612 A1* | 3/2013 | Arao | .................... | G02B 6/4477 385/77 |

(Continued)

FOREIGN PATENT DOCUMENTS

| | | |
|---|---|---|
| JP | 2011-177264 A | 9/2011 |
| JP | 2014-56649 A | 3/2014 |
| JP | 2016-209542 A | 12/2016 |

OTHER PUBLICATIONS

International Search Report and Written Opinion dated Feb. 22, 2021, received for PCT Application PCT/JP2021/002295, filed on Jan. 22, 2021, 8 pages including English Translation.

*Primary Examiner* — Jerry M Blevins
(74) *Attorney, Agent, or Firm* — XSENSUS LLP (57) ABSTRACT

Provided is a medical observation system capable of preventing disconnection of metal cables without increasing the thickness of a braided shield wire. The medical observation system includes a transmission cable including: an optical cable having one or more optical fiber cores; a plurality of metal cables arranged around the optical cable; and a tension member made of a high-strength fiber, and disposed in parallel with an extending direction of the optical cable.

23 Claims, 9 Drawing Sheets

(56) References Cited

U.S. PATENT DOCUMENTS

2016/0254075 A1 9/2016 Huang et al.
2017/0108658 A1* 4/2017 Kondo ................. G02B 6/4471

* cited by examiner

MEDICAL OBSERVATION SYSTEM AND TRANSMISSION CABLE

CROSS-REFERENCE TO RELATED APPLICATIONS

The present application is based on PCT filing PCT/JP2021/002295, filed Jan. 22, 2021, which claims priority to JP 2020-042475, filed Mar. 11, 2020, the entire contents of each are incorporated herein by reference.

FIELD

The present disclosure relates to a medical observation system and a transmission cable.

BACKGROUND

Conventionally, in the medical field, endoscope devices are used for observation of an organ inside a subject such as a patient. An endoscope device includes, for example, an endoscope including an imaging element (hereinafter, referred to as a camera head), a control device that controls the operation of the camera head, processes an image signal captured by the imaging element, and causes a display device to display an image of the inside of a subject, and a transmission cable that electrically connects the camera head and the control device and transmits various signals.

In recent years, imaging elements having a large number of pixels that enable more delicate image observation have been developed, and application of the imaging elements to endoscope devices has been examined. Accordingly, in order to transmit large-capacity signals between an imaging element and a control device at high speed, adoption of optical transmission systems that transmit signals using laser light has been studied (see, for example, Patent Literature 1).

CITATION LIST

Patent Literature

Patent Literature 1: JP 2016-209542 A

SUMMARY

Technical Problem

In Patent Literature 1 described above, in a transmission cable, the periphery of an optical cable and a plurality of metal cables is covered with a braided shield wire, thereby preventing noise from entering a signal to be transmitted, and the strength of the braided shield wire reduces a stress load applied to the optical cable or the metal cables.

However, as the diameters of the metal cables are reduced, the stress applied to the metal cables cannot be reduced only by the strength of the braided shield wire, and there is a risk of disconnection. Meanwhile, in order to prevent disconnection of the metal cables, it is conceivable to increase the strength of the braided shield wire, that is, to increase the thickness of the braided shield wire; however, there is a problem that the outer diameter of the transmission cable increases which impairs flexibility and bendability.

The present disclosure has been made in view of the above, and an object of the present disclosure is to provide a medical observation system and a transmission cable capable of preventing disconnection of metal cables without increasing the thickness of a braided shield wire.

Solution to Problem

To solve the above-described problem and achieve the object, a medical observation system according to the present disclosure includes a transmission cable including: an optical cable including one or more optical fiber cores; a plurality of metal cables arranged around the optical cable; and a tension member made of a high-strength fiber, and disposed in parallel with an extending direction of the optical cable.

Moreover, a transmission cable according to the present disclosure includes: an optical cable including one or more optical fiber cores; a plurality of metal cables arranged around the optical cable; and a tension member made of a high-strength fiber, and disposed in parallel with an extending direction of the optical cable.

Advantageous Effects of Invention

According to the present disclosure, it is possible to prevent disconnection of metal cables while maintaining the outer diameter, flexibility, and bendability of a transmission cable can be achieved.

DESCRIPTION OF EMBODIMENTS

Hereinafter, modes for carrying out the present disclosure will be described in detail together with the drawings. Note that the present disclosure is not limited by the following embodiments. In addition, each of the drawings referred to in the following description merely schematically illustrates the shape, the size, and the positional relationship to an extent that the content of the present disclosure can be understood. That is, the present disclosure is not limited only to the shape, the size, nor the positional relationship illustrated in each of the drawings. In addition, in description of the drawings, the same part is denoted by the same symbol and thereby described.

First Embodiment

Figure 1:
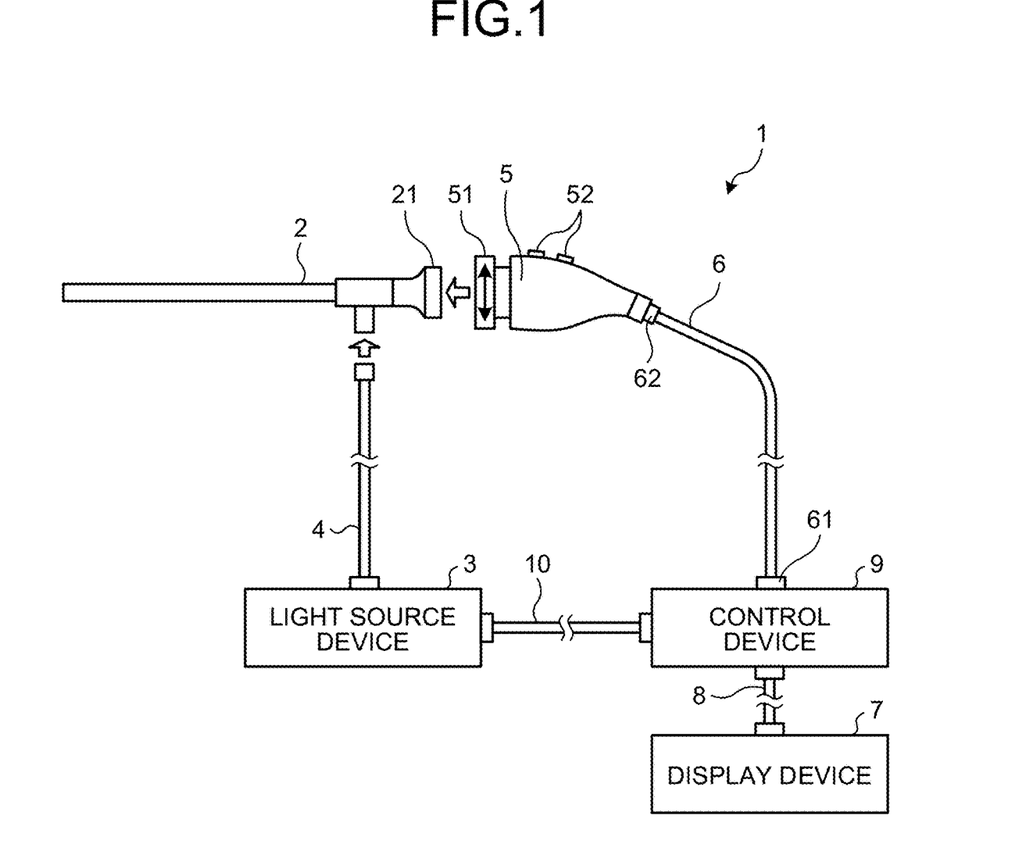
FIG. 1 is a diagram illustrating a schematic configuration of a medical observation system according to a first embodiment.

FIG. 1 is a diagram illustrating a schematic configuration of a medical observation system 1 according to a first embodiment. The medical observation system 1 illustrated in FIG. 1 is used in the medical field and observes a subject by being inserted in a living body of a subject such as a living body of a human or an animal and displaying an image capturing the inside thereof. Note that, in the first embodiment, a rigid endoscope system using a rigid endoscope (insertion unit 2) illustrated in FIG. 1 will be described as the medical observation system 1; however, it is not limited thereto, and for example, a flexible endoscope system may be used.

The medical observation system 1 illustrated in FIG. 1 includes the insertion unit 2, a light source device 3, a light guide 4, a camera head 5 (endoscope imaging device), a first transmission cable 6, a display device 7, a second transmission cable 8, a control device 9, and a third transmission cable 10.

The insertion unit 2 is rigid or at least partially flexible and has an elongated shape. The insertion unit 2 is inserted into a subject such as a patient. The insertion unit 2 includes one or a plurality of lenses therein and includes an optical system that forms an observation image.

The light source device 3 is connected with one end of the light guide 4. Under control by the control device 9, the light source device 3 emits (supplies), to the one end of the light guide 4, white light for illuminating the inside of the subject and excitation light or infrared light to a chemical agent administered to or scattered on the subject. The light source device 3 includes a light emitting diode (LED) light source or a semiconductor laser element such as a laser diode (LD). The light source device 3 and the control device 9 may be configured so as to communicate individually as illustrated in FIG. 1 or may be integrated.

The one end of the light guide 4 is detachably connected to the light source device 3, and the other end is detachably connected to the insertion unit 2. The light guide 4 guides light emitted from the light source device 3 from the one end to the other end and supplies the light to the insertion unit 2.

The camera head 5 is detachably connected to an eyepiece unit 21 of the insertion unit 2. Under the control by the control device 9, the camera head 5 generates image data (imaging signal) by capturing an observation image formed by the insertion unit 2 and outputs the image data. In addition, the camera head 5 includes an operation ring unit 51 provided so as to be rotatable in the circumferential direction and a plurality of input units 52 that receives input of instruction signals for instructing various operations of the medical observation system 1.

One end of the first transmission cable 6 is detachably connected to the control device 9 via a first connector unit 61, and the other end is connected to the camera head 5 via a second connector unit 62. The first transmission cable 6 transmits image data output from the camera head 5 to the control device 9 and transmits a control signal, a synchronization signal, a clock signal, power, and the like output from the control device 9 to the camera head 5. The first transmission cable 6 functions as a transmission cable of the present disclosure. The first transmission cable 6 will be described in detail later.

The display device 7 can be connected to the control device 9 via the second transmission cable 8 and displays a display image based on the image data processed by the control device 9 under the control by the control device 9.

One end of the second transmission cable 8 is detachably connected to the display device 7, and the other end is detachably connected to the control device 9. The second transmission cable 8 transmits, to the display device 7, the display image based on the image data processed by the control device 9.

The control device 9 includes a memory and a processor including hardware such as a central processing unit (CPU), a graphics processing unit (GPU), an application specific integrated circuit (ASIC), and a field programmable gate array (FPGA). The control device 9 comprehensively controls the operation of the camera head 5, the display device 7, and the light source device 3 via the first transmission cable 6, the second transmission cable 8, and the third transmission cable 10, respectively, in accordance with a program recorded in the memory. In addition, the control device 9 performs various types of image processing on the image data input from the camera head 5 via the first transmission cable 6 and outputs the image data to the second transmission cable 8.

One end of the third transmission cable 10 is detachably connected to the light source device 3, and the other end is detachably connected to the control device 9. The third transmission cable 10 transmits a control signal from the control device 9 to the light source device 3.

Figure 2:
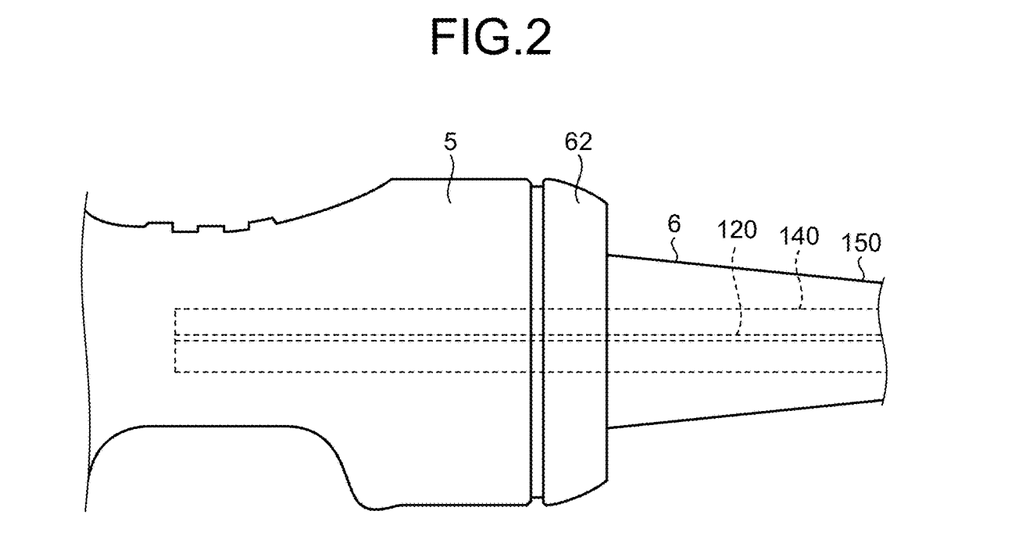
FIG. 2 is a side view of the vicinity of a connector of a first transmission cable included in the medical observation system according to the first embodiment.
Figure 3:
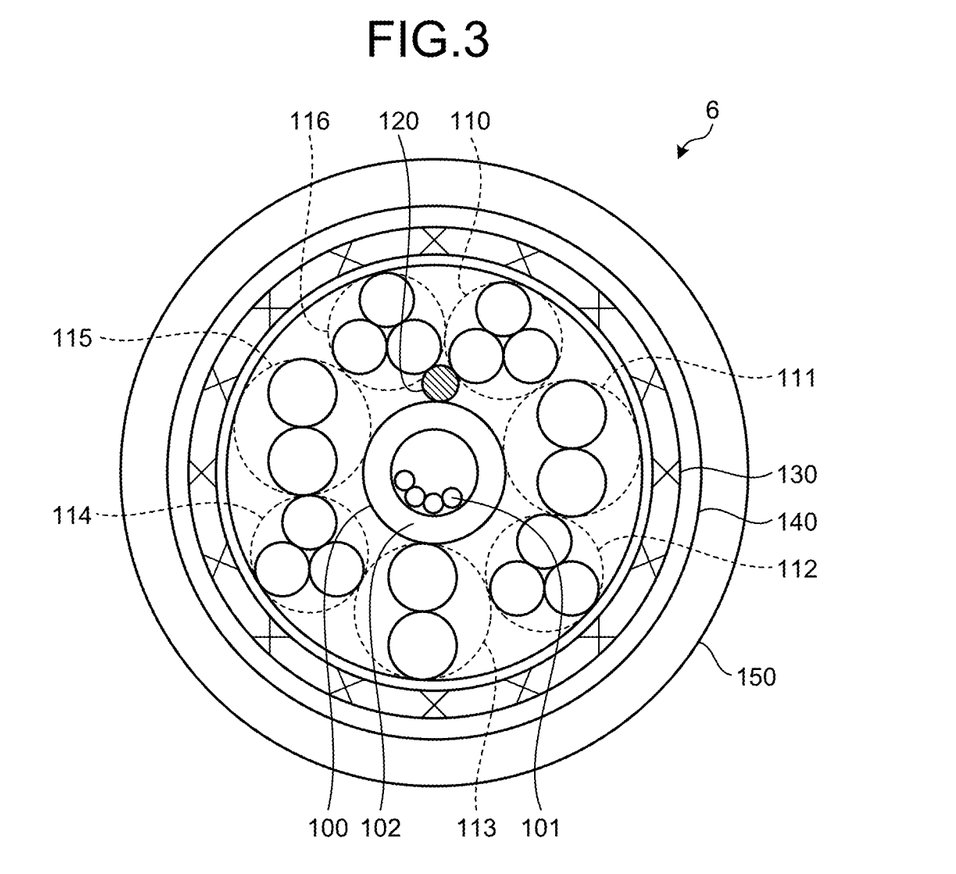
FIG. 3 is a cross-sectional view of the first transmission cable.

Next, the first transmission cable 6 will be described. FIG. 2 is a side view of the vicinity of the second connector unit 62 of the first transmission cable 6 included in the medical observation system 1 according to the first embodiment. FIG. 3 is a cross-sectional view of the first transmission cable 6.

The first transmission cable 6 includes an optical cable 100 having one or more optical fiber cores 101, a plurality of metal cables 110, 111, 112, 113, 114, 115, and 116 arranged around the optical cable 100, and a tension member 120 made of a high-strength fiber and arranged in parallel with the extending direction of the optical fiber cores 101.

The optical cable 100 has a structure in which the optical fiber cores 101, linearly extending, are covered with a sheath 102. The metal cables 110, 112, 114, and 116 have a structure in which metal wires having a small diameter are spirally twisted, and the metal cables 111, 113, and 115 have a structure in which metal wires having a large diameter are spirally twisted.

In the first transmission cable 6, the metal cables 110 to 116 are spirally arranged around the optical cable 100, and the periphery of the metal cables 110 to 116 is covered with a braided shield wire 130 and an insulating sheath 140. The outer periphery of the sheath 140 is covered with an exterior covering 150.

The tension member 120 has an outer diameter similar to that of the metal wire included in the metal cables 110 to 116 and is formed of an insulating fiber having high strength. Examples of the material include para-aramid fibers, high-molecular weight polyethylene fibers, high-strength polyarylate fibers, and polyparaphenylene benzobis oxazole fibers; however, high-strength polyarylate fibers that do not absorb water and have excellent dimensional stability are preferably used. The tension member 120 is disposed between the optical cable 100 and the metal cables 110 to 116. As illustrated in FIG. 2, the tension member 120 extends from the distal end side to the proximal end side along the axial direction of the first transmission cable 6. Arranging the tension member 120 in the first transmission cable 6 can prevent disconnection of the optical fiber cores 101 and the metal wires. In addition, since the tension member 120 is disposed in a gap generated between the optical cable 100 and the metal cables 110 to 116, the diameter of the first transmission cable 6 can be reduced, and the influence on the tension member 120 when the first transmission cable 6 is subjected to autoclave sterilization can be reduced. Furthermore, since the tension member 120 is fixed by the metal cables 110 to 116 spirally arranged around the optical cable 100, it is easy to manufacture.

Figure 4A:
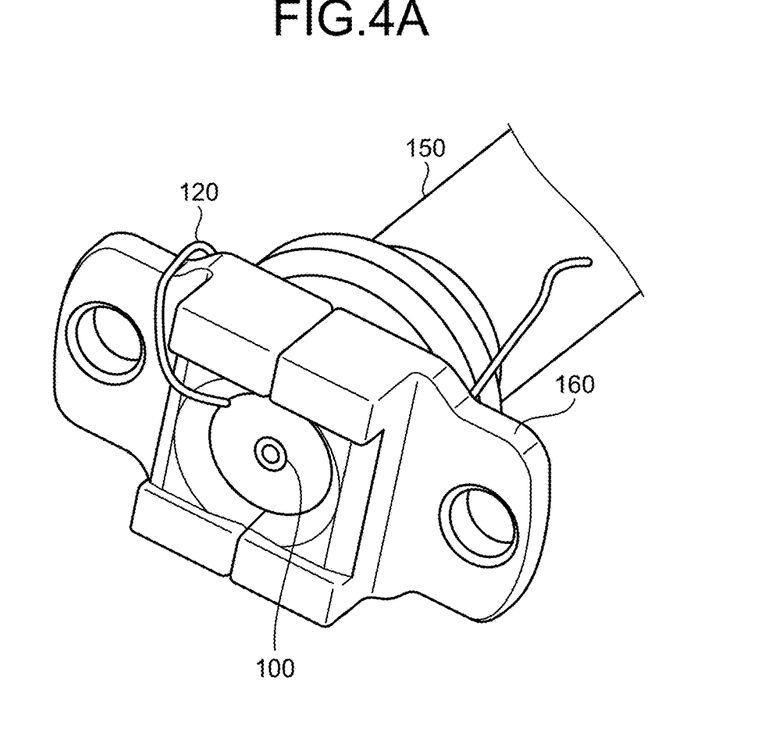
FIG. 4A is a diagram for describing a method of fixing a tension member inside the connector of the first transmission cable.
Figure 4B:
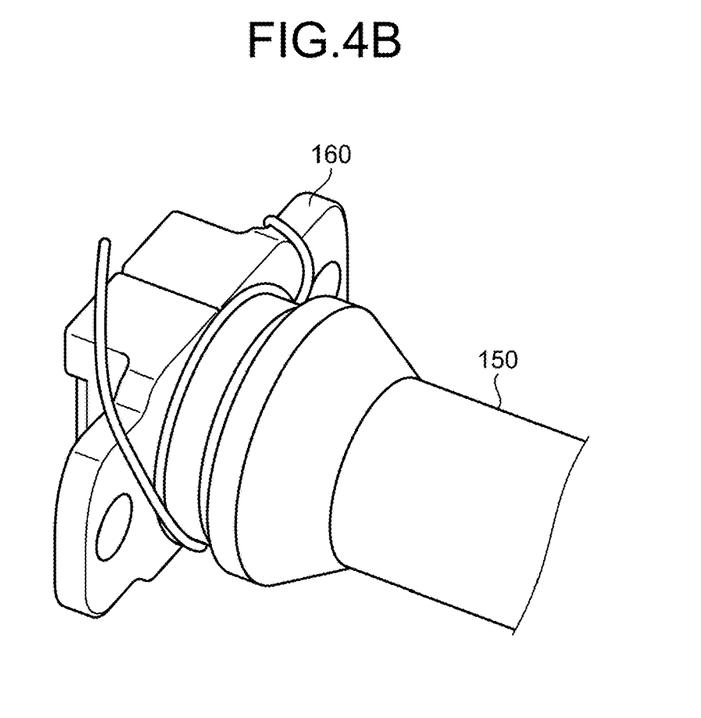
FIG. 4B is a diagram for describing the method of fixing the tension member inside the connector of the first transmission cable.
Figure 4C:
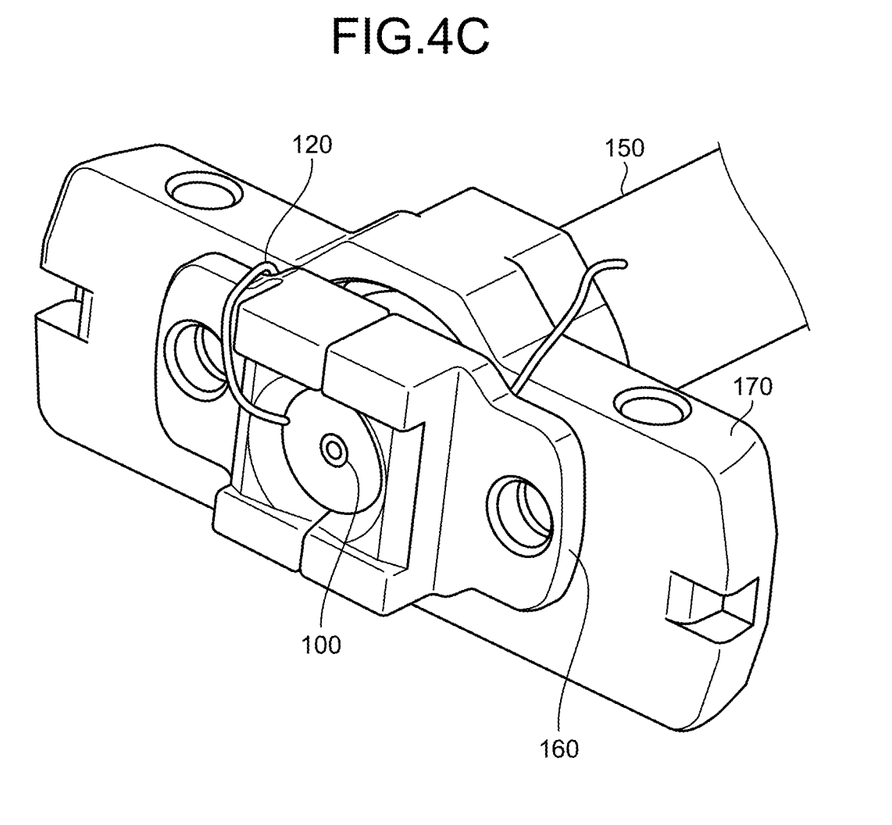
FIG. 4C is a diagram for describing the method of fixing the tension member inside the connector of the first transmission cable.

The tension member 120 is pulled out from the braided shield wire 130 and the sheath 140 at an end thereof and is fixed to a component included in the second connector unit 62. FIGS. 4A to 4C are diagrams for explaining a method of fixing the tension member 120 in the second connector unit 62 of the first transmission cable 6.

The tension member 120 is pulled out from the braided shield wire 130 and the sheath 140, wound around a first component 160 included in the second connector unit 62, and then clamped by a second component 170 disposed on a proximal end side of the first component 160, and thereby fixed. By fixing the tension member 120 to the component included in the second connector unit 62, disconnection of the optical fiber cores 101 and the metal wires at the end can be prevented. Note that, also on the first connector unit 61 side, the tension member 120 is pulled out from the braided shield wire 130 and the sheath 140 and is fixed to a component included in the first connector unit 61.

Figure 5:
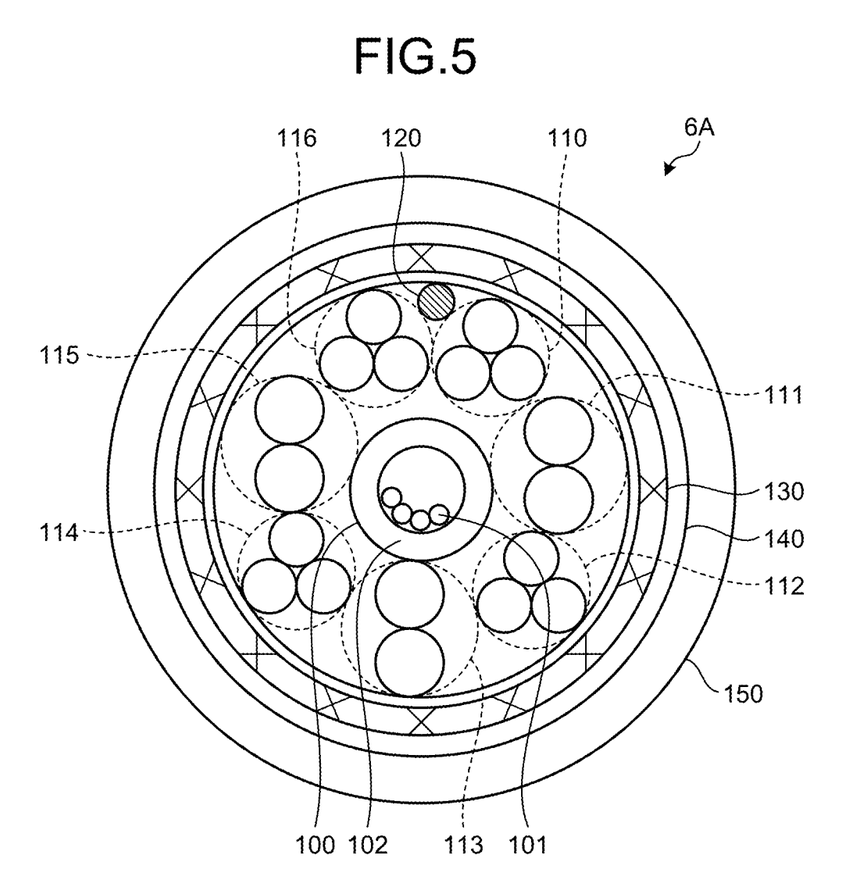
FIG. 5 is a cross-sectional view of a first transmission cable according to a first modification of the first embodiment.

Although the first embodiment has been described above, and it is preferable that the tension member 120 be disposed between the optical cable 100 and the metal cables 110 to 116 from the viewpoint of manufacturing and autoclave resistance; however, it is not limited thereto. FIG. 5 is a cross-sectional view of a first transmission cable 6A according to a first modification of the first embodiment. In the first transmission cable 6A, a tension member 120 is arranged on the outer periphery of metal cables 110 to 116.

Figure 6:
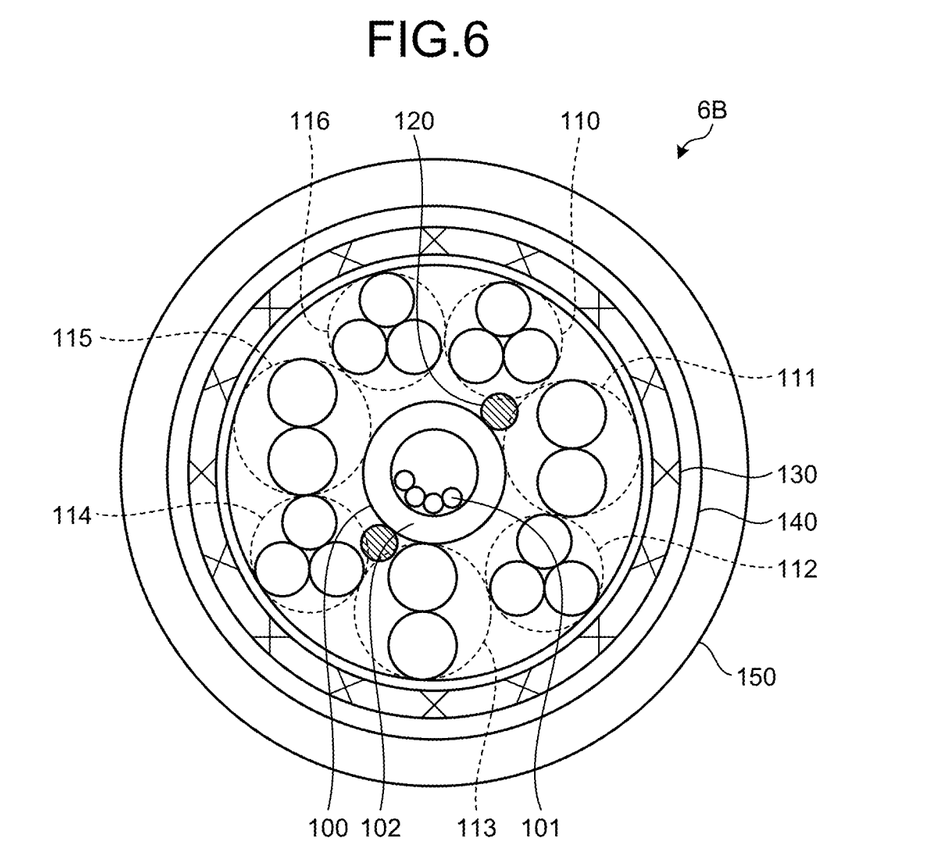
FIG. 6 is a cross-sectional view of a first transmission cable according to a second modification of the first embodiment.
Figure 7:
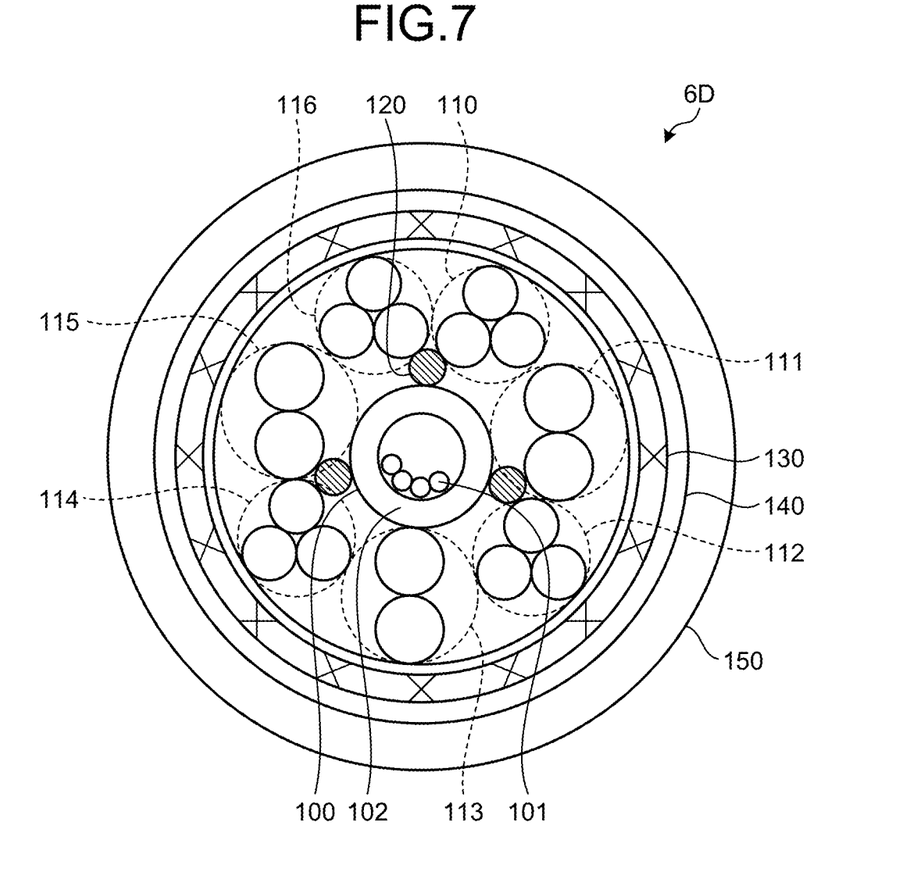
FIG. 7 is a cross-sectional view of a first transmission cable according to a third modification of the first embodiment.

In addition, in the first embodiment, one tension member 120 is disposed in the first transmission cable 6; however, it is not limited thereto. FIG. 6 is a cross-sectional view of a first transmission cable 6B according to a second modification of the first embodiment, and FIG. 7 is a cross-sectional view of a first transmission cable 6D according to a third modification of the first embodiment.

In the first transmission cable 6B according to the second modification, two tension members 120 face each other, that is, are arranged rotationally symmetrically about an optical cable 100. Meanwhile, in the first transmission cable 6D according to the third modification, three tension members 120 are arranged at the same intervals (every 120°), that is, rotationally symmetrically about an optical cable 100. By installing the plurality of tension members 120, it is possible to effectively prevent disconnection of the optical cable 100 or the metal cables 110 to 116.

Second Embodiment

Next, a second embodiment will be described. In the first embodiment described above, a case of application to a rigid endoscope system using a rigid endoscope has been described; however, in the second embodiment, a case of application to a flexible endoscope system using a flexible endoscope will be described. Note that the same components as those of the endoscope system 1 according to the first embodiment described above are denoted by the same symbols, and detailed description thereof will be omitted.

Figure 8:
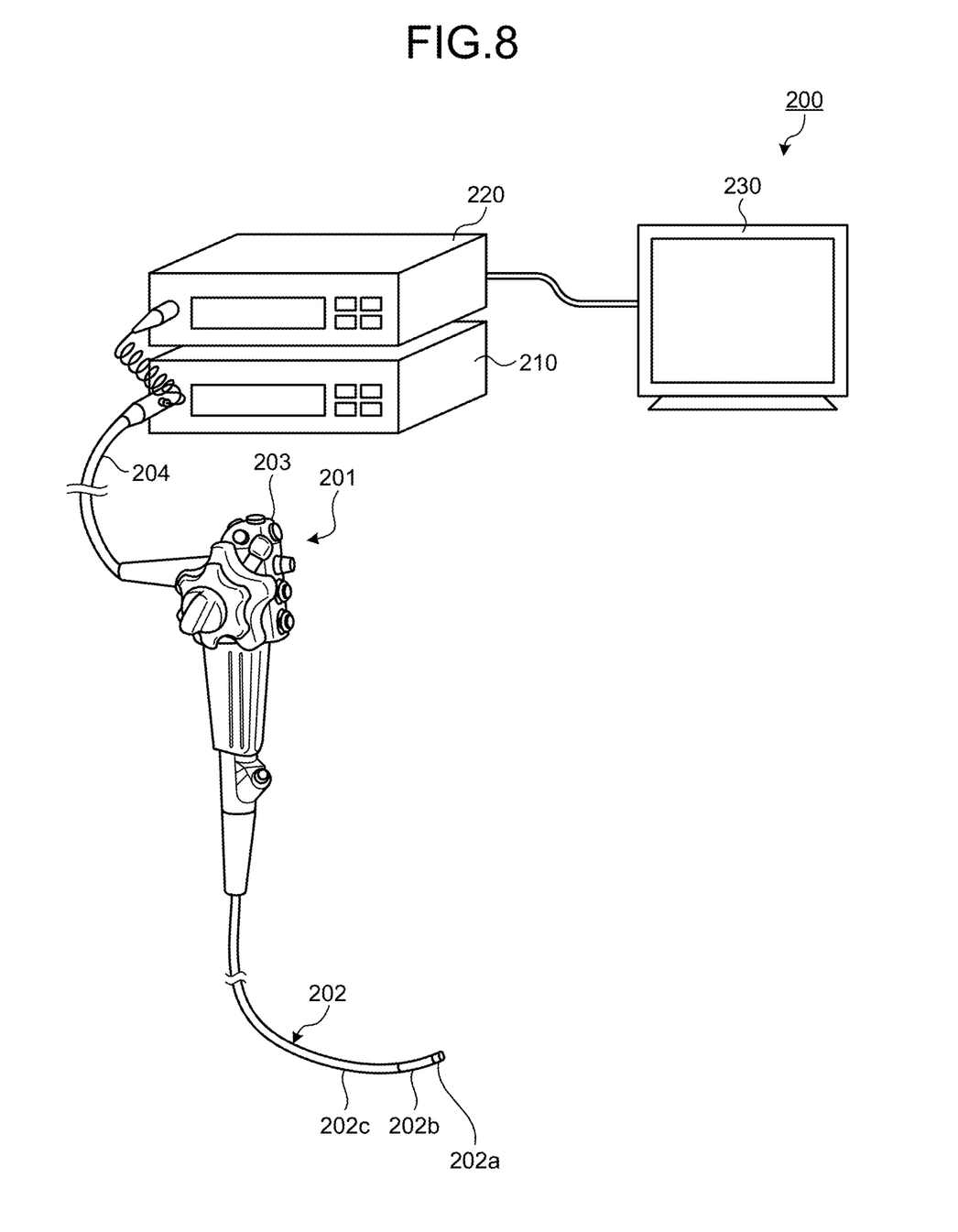
FIG. 8 is a diagram illustrating a schematic configuration of a medical observation system according to a second embodiment.

FIG. 8 is a diagram illustrating a schematic configuration of a medical observation system 200 according to the second embodiment. The medical observation system 200 illustrated in FIG. 8 includes an endoscope 201 that generates image data by capturing an in-vivo image of an observed region with an insertion unit 202 inserted into a subject, a light source device 210 that supplies white light or infrared light to the endoscope 201, a control device 220 that performs predetermined image processing on an imaging signal acquired by the endoscope 201 and comprehensively controls the operation of the entire medical observation system 200, and a display device 230 that displays the in-vivo image subjected to the image processing by the control device 220.

The endoscope 201 includes, as illustrated in FIG. 8, the insertion unit 202 that is flexible and has a long thin shape, an operating unit 203 connected to a proximal end side of the insertion unit 202 and receives input of various operation signals, and a universal cord 204 extending in a different direction from a direction in which the insertion unit 202 extends from the operating unit 203, the universal cord 204 to be connected to the light source device 210 and the control device 220. The universal cord 204 functions as a transmission cable of the present disclosure.

The insertion unit 202 includes a distal end 202a incorporating an imaging unit (not illustrated) that captures the inside of a living body and generates an image signal, a bendable portion 202b including a plurality of bending pieces, the bendable portion 202b freely bendable, and a flexible tube portion 202c flexible and having an elongated shape, the flexible tube portion 202c connected to a proximal end side of the bendable portion 202b.

The universal cord 204 includes a configuration similar to that of the first transmission cable 6 described in the first embodiment. A plurality of transmission image signals (optical signals) processed (generated) in the operating unit 203 is output to the control device 220 via the universal cord 204.

Even in the case of using the medical observation system 200 as in the second embodiment described above, similar effects to those of the first embodiment described above are achieved.

Third Embodiment

Next, a third embodiment will be described. In the first and second embodiments described above, application is made to medical observation systems; however, in the third embodiment, the present invention is applied to a surgical microscope that enlarges and captures a predetermined field of view in a subject (in a living body) or a surface of a subject (surface of a living body). Note that the same components as those of the medical observation system 1 according to the first embodiment described above are denoted by the same symbols, and detailed description thereof will be omitted.

Figure 9:
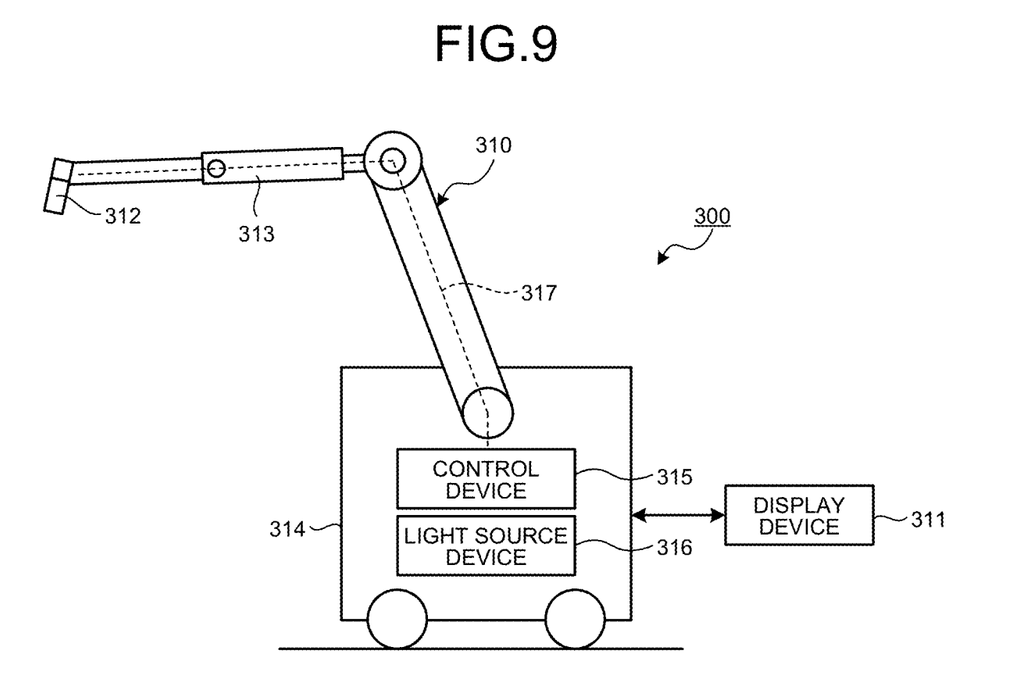
FIG. 9 is a diagram illustrating a schematic configuration of a medical observation system according to a third embodiment.

FIG. 9 is a diagram illustrating a schematic configuration of a medical observation system 300 according to the third embodiment of the invention. As illustrated in FIG. 9, the medical observation system 300 according to the third embodiment includes a surgical microscope 310 that captures an image for observing a subject to generate an image signal and generates a plurality of transmission image signals from the image signal, a control device 315 (the control device described in the first embodiment or the second embodiment) that receives the plurality of transmission image signals generated by the surgical microscope 310 and processes the plurality of transmission image signals, and a display device 311 that displays an image based on a video signal processed by the control device 315.

The surgical microscope 310 includes a microscope unit 312 that enlarges and captures a minute portion of a subject, generates an image signal, and generates a plurality of transmission image signals from the image signal, a support unit 313 that is connected to a proximal end of the microscope unit 312 and includes an arm that rotatably supports the microscope unit 312, and a base unit 314 that rotatably holds the proximal end of the support unit 313 and is movable on a floor surface. The control device 315 is installed in the base unit 314. Note that the base unit 314 may be fixed to a ceiling, a wall, or the like so as to support the support unit 313 instead of being movably provided on a floor surface. Furthermore, the base unit 314 may include a light source unit that generates illumination light to be emitted from the surgical microscope 310 to a subject.

Although not specifically illustrated, the microscope unit 312 includes an imaging unit that captures the inside of a living body or a surface of the living body and generates an image signal, a transmission signal processing unit, and an E/O converter, and the image signal generated by the imaging unit is processed by the transmission signal processing unit. Then, a plurality of transmission image signals (optical signals) processed (generated) by the microscope unit 312 (the transmission signal processing unit and an electro-optical converter) is output to the control device 315 via a transmission cable 317 disposed inside the support unit 313 along the support unit 313.

Even in the case of using the surgical microscope 310 as in the third embodiment described above, similar effects to those of the first embodiment described above are achieved.

Although some of embodiments of the present application have been described in detail with reference to the drawings, these are merely examples, and the present invention can be implemented in other modes with various modifications and improvements on the basis of the knowledge of those skilled in the art in addition to the aspects described in the disclosure of the present invention.

Note that the present disclosure can also have the following configurations.

(1) A medical observation system including a transmission cable including: an optical cable including one or more optical fiber cores; a plurality of metal cables arranged around the optical cable; and a tension member made of a high-strength fiber, and disposed in parallel with an extending direction of the optical cable.
(2) The medical observation system according to (1), wherein the metal cables are arranged so as to form a spiral structure around the optical cable, and the tension member is disposed between the optical cable and the metal cables.
(3) The medical observation system according to (1) or (2), wherein a periphery of the optical cable, the metal cables, and the tension member is covered with a braided shield wire.
(4) The medical observation system according to any one of (1) to (3), wherein a plurality of the tension members is arranged rotationally symmetrically around the optical cable.
(5) The medical observation system according to any one of (1) to (4), wherein a connector unit is disposed at an end of the transmission cable, and an end of the tension member is fixed to a component included in the connector unit.
(6) The medical observation system according to (5), wherein the component included in the connector unit includes a first component and a second component, and the tension member is fixed by being wound around the first component and clamped by the second component.
(7) A transmission cable including: an optical cable including one or more optical fiber cores; a plurality of metal cables arranged around the optical cable; and a tension member made of a high-strength fiber, and disposed in parallel with an extending direction of the optical cable.

REFERENCE SIGNS LIST 1, 200, 300 Medical Observation System
2, 202 Insertion Unit
3, 210, 316 Light Source Device
4 Light Guide
5 Camera Head
6 First Transmission Cable
7, 230, 311 Display Device
8 Second Transmission Cable
9, 220, 315 Control Device
10 Third Transmission Cable
21 Eyepiece Unit
61 First Connector Unit
62 Second Connector Unit
201 Endoscope
203 Operating Unit
204 Universal Cord
310 Surgical Microscope
312 Microscope Unit
313 Support Unit
314 Base Unit
317 Transmission Cable

The invention claimed is:
1. A medical observation system comprising
a transmission cable including:
   an optical cable including one or more optical fiber cores;
   a plurality of metal cables arranged around the optical cable; and
   a tension member made of an insulating fiber, disposed in parallel with an extending direction of the optical cable, and in a first gap between the optical cable and the metal cables or in a second gap between the metal cables and an outer periphery of the transmission cable.
2. The medical observation system according to claim 1, wherein
   the metal cables are arranged so as to form a spiral structure around the optical cable, and
   the tension member is disposed between the optical cable and the metal cables.
3. The medical observation system according to claim 1, wherein a periphery of the optical cable, the metal cables, and the tension member is covered with a braided shield wire.
4. The medical observation system according to claim 1, wherein a plurality of the tension members is arranged rotationally symmetrically around the optical cable in a corresponding plurality of gaps.

5. The medical Observation system according to claim 1, wherein
   a connector is disposed at an end of the transmission cable, and
   an end of the tension member is fixed to the connector.

6. The medical observation system according to claim 5, wherein
   the component included in the connector includes a first component and a second component, and
   the tension member is fixed by being wound around the first component and clamped by the second component.

7. The medical observation system according to claim 1, wherein the tension member is between the optical cable and the metal cables.

8. The medical observation system according to claim 1, further comprising a shield that surrounds the optical cable, the metal cables and the tension member.

9. The medical observation system according to claim 1, further comprising a shield that surrounds the optical cable and the metal cables.

10. The medical observation system according to claim 9, wherein the second gap is between the metal cables and the shield.

11. The medical observation system according to claim 9, wherein the tension member extends through the shield.

12. The medical observation system according to claim 1, wherein an outer diameter of the transmission cable is maintained with the inclusion of the tension member.

13. The medical observation system according to claim 1, wherein the tension member is made of high-strength insulating fiber.

14. The medical observation system according to claim 1, wherein the insulating fiber has at least one of para-aramid fiber, polyethylene fiber, polyarylate fiber, and polyparaphenylene benzobis oxazole fiber.

15. A transmission cable comprising:
   an optical cable including one or more optical fiber cores;
   a plurality of metal cables arranged around the optical cable; and
   a tension member made of an insulating fiber, disposed in parallel with an extending direction of the optical cable and in a first gap between the optical cable and the metal cables or in a second gap between the metal cables and an outer periphery of the transmission cable.

16. The transmission cable according to claim 15, wherein a plurality of the tension members is arranged rotationally symmetrically around the optical cable in a corresponding plurality of gaps.

17. The transmission cable according to claim 15, further comprising a shield that surrounds the optical cable, the metal cables and the tension member.

18. The transmission cable according to claim 15, further comprising a shield that surrounds the optical cable and the metal cables.

19. The transmission cable according to claim 18, wherein the second gap is between the metal cables and the shield.

20. The transmission cable according to claim 18, wherein the tension member extends through the shield.

21. The transmission cable according to claim 15, wherein an outer diameter of the transmission cable is maintained with the inclusion of the tension member.

22. The transmission cable according to claim 15, wherein the tension member is made of high-strength insulating fiber.

23. The transmission cable according to claim 15, wherein the insulating fiber has at least one of para-aramid fiber, polyethylene fiber, polyarylate fiber, and polyparaphenylene benzobis oxazole fiber.

* * * * *